United States Patent [19]
Nemphos et al.

[11] Patent Number: 5,886,055
[45] Date of Patent: Mar. 23, 1999

[54] PROCESS FOR PRODUCTION OF METHANOL

[75] Inventors: Speros P. Nemphos; Willibrord A. Groten; John R. Adams, all of Pasadena, Tex.

[73] Assignee: Catalytic Distillation Technologies, Pasadena, Tex.

[21] Appl. No.: 782,128

[22] Filed: Jan. 13, 1997

[51] Int. Cl.[6] .......................... C07C 27/10; C07C 205/00
[52] U.S. Cl. ............................................ 518/700; 518/713
[58] Field of Search .......................... 568/840; 252/373; 518/700, 713

[56] References Cited

U.S. PATENT DOCUMENTS

| | | | |
|---|---|---|---|
| 4,031,123 | 6/1977 | Espino et al. | 260/449.5 |
| 4,475,005 | 10/1984 | Paret et al. | 568/697 |
| 4,766,155 | 8/1988 | Sun et al. | 518/713 |
| 4,780,481 | 10/1988 | Courty et al. | 518/713 |
| 4,847,430 | 7/1989 | Quang et al. | 568/697 |
| 5,087,780 | 2/1992 | Arganbright | 585/259 |
| 5,198,196 | 3/1993 | Jones, Jr. | 422/219 |
| 5,266,546 | 11/1993 | Hearn | 502/300 |
| 5,338,517 | 8/1994 | Evans, III et al. | 422/191 |
| 5,431,890 | 7/1995 | Crossland et al. | 422/211 |

OTHER PUBLICATIONS

Commercial–Scale Demonstration of a Liquid–Phase Menthonol Process, Steven L. Cook, Eastman Chemical Company, ACS Div Fuel Chem. v. 40 (1) –pp. 124–128.

Liquid–Phase Methanol Synthesis: Catalysts, Mechanism Kinetics, Chemical Equilibria, and Modeling–A Review Andrzej Cybulski, Catal. Rev. Sci. Eng. 36(4) 557–615 (1994).

*Primary Examiner*—Gary Geist
*Assistant Examiner*—Karl J. Puttlitz, Jr.
*Attorney, Agent, or Firm*—Kenneth H. Johnson

[57] ABSTRACT

A process for the production of methanol is disclosed wherein the gaseous reactants of CO, $H_2$ and optimally $CO_2$ are reacted in a distillation column reactor in the presence of an inert $C_7$–$C_{12}$ component, which is boiling at the reaction temperature within the catalyst bed. The inert component is taken overhead along with the methanol and separated therefrom for reflux of the inert component back to the reactor.

15 Claims, 1 Drawing Sheet

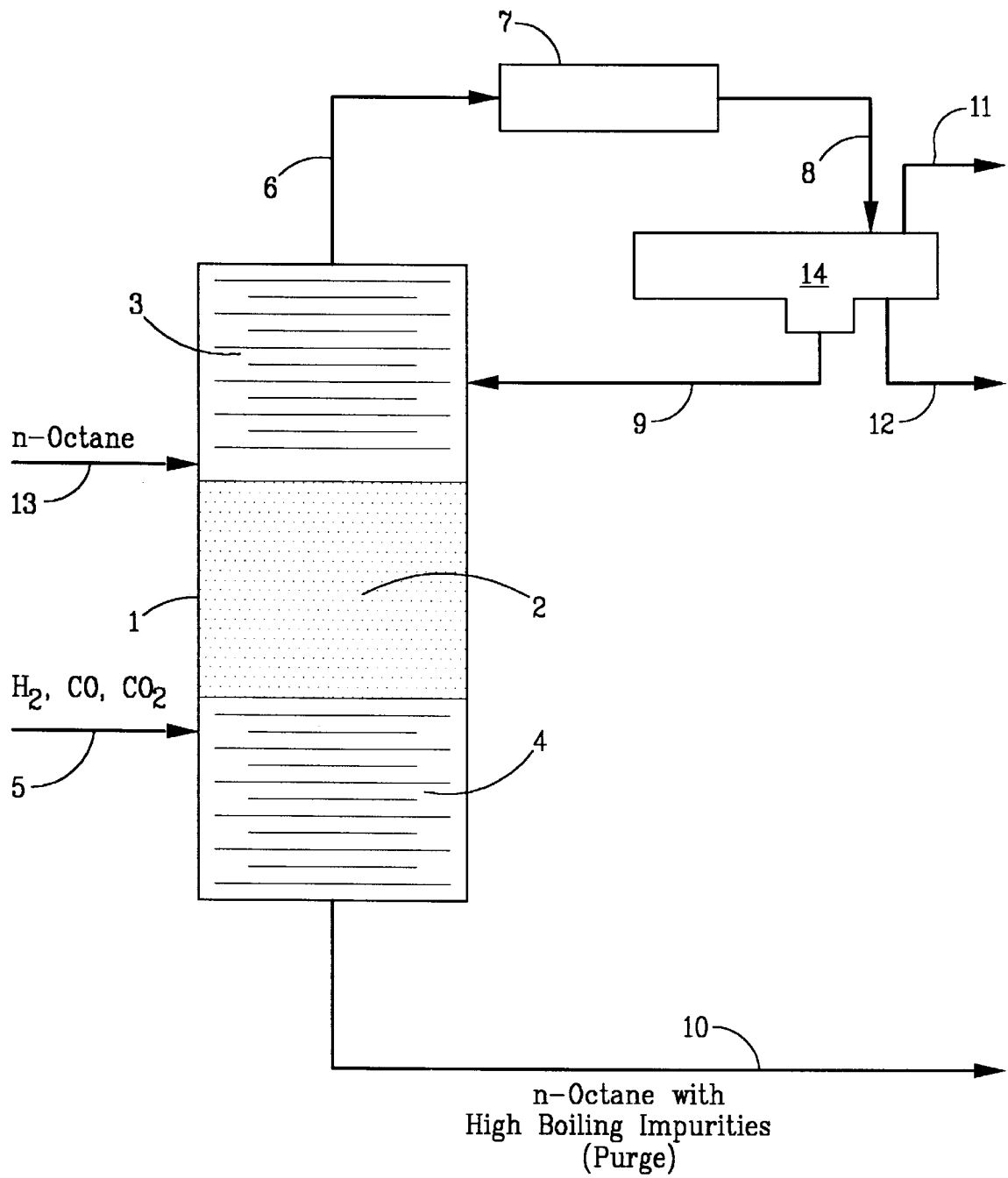

PROCESS FOR PRODUCTION OF METHANOL

BACKGROUND OF THE INVENTION

1. Field of the Invention

The present invention relates generally to the production of methanol from the reaction of carbon monoxide and carbon dioxide with hydrogen in the presence of a copper/zinc/alumina catalyst and in particular in a catalytic distillation process. More particularly, the invention relates to the use of an inert component in a catalytic distillation column wherein the inert component is boiling and condensing around the normally gaseous reactants.

2. Related Art

Methanol is one of the basic chemicals and as such is produced at an annual rate of over 10 million tons. Conventionally methanol has been produced in two-phase systems: The reactants (CO, $CO_2$, and $H_2$) and products (mainly $CH_3OH$ and $H_2O$) forming the gas phase and the catalyst being the solid phase. In a methanol plant, the reaction of carbon monoxide, carbon dioxide and hydrogen is exothermic. Thus in a conventional fixed bed reactor design, heat control and removal is of prime importance. If too much $CO_2$ or CO is present, the reactor can overheat and damage the catalyst. As a result, for a given catalyst, a liquid phase reactor was preferable under the prior technology, because the basic characteristics of a liquid phase reactor allow it to be cooled internally.

More recently a three-phase methanol synthesis process (now known under the trademark LPMEOH) has been developed. In that process an inert liquid phase is introduced into the reactor, mainly to absorb heat released during the reaction. Heat transfer between the solid catalyst and the liquid phase is highly efficient, thereby allowing higher conversions to be obtained without impairment of catalyst activity. The liquid phase allows for the removal of heat by use of an internal heat exchanger in the LPMEOH process. The solid particulate catalyst is introduced in a slurry of the inert liquid.

The following three equations may be used to empirically represent the reactions going on during the present process:

(1)

(2)

(3)

Catalytic distillation, in which reaction products are produced and concurrently separated from reactants by distillation, has been used successfully to control temperatures in exothermic reactions. However, the use of catalytic distillation has been traditionally limited by the fact that one of the reactants must be a boiling liquid at the conditions inside the reactor. In the earlier catalytic distillation processes both reactants were fed to the reactor as liquids. More recently, U.S. Pat. No. 5,087,780 has shown that the catalytic distillation method is useful in a process wherein hydrogen is a reaction component. Inert materials have been fed to a catalytic distillation for various purposes, such as to provide a heat sink, but always one of the reactants has been a boiling liquid

SUMMARY OF THE INVENTION

In order to take advantage of the characteristic traits of catalytic distillation while reacting the normally gaseous reactants of CO, $CO_2$ and H2, the present invention contemplates utilizing an inert condensing medium or component for the reactants. The inert condensing component can be fed separately or intermingled with the gaseous feed. It is proposed that at least one reactant is at least partially occluded in said inert condensing component and said reactant being a vapor at the conditions within said reactor.

The invention can be described as a process comprising:

(a) feeding an inert condensing component as a liquid stream to a distillation column reactor having a distillation reaction zone, said inert condensing component boiling at the conditions within said distillation column reactor;

(b) feeding CO and $H_2$ or CO, $CO_2$ and $H_2$ to a distillation column reactor; and (c) concurrently in said distillation column reactor
  (i) boiling said inert condensing component and refluxing said inert condensing component such that a portion of said inert component is condensing in said distillation reaction zone;
  (ii) contacting said CO and $H_2$ or CO, $CO_2$ and $H_2$ and said inert condensing component with a solid particulate catalyst in said distillation reaction zone, under conditions within said reactor at which said CO, $CO_2$ and $H_2$ are in the vapor state, and reacting a portion of said CO and/or $CO_2$ and $H_2$ to form methanol, and
  (iii) removing an overheads containing methanol, inert condensing agent and unreacted CO, $CO_2$ or hydrogen and (d) separating said methanol from said carbon monoxide, carbon dioxide or hydrogen.

BRIEF DESCRIPTION OF THE DRAWING

The FIGURE is a flow diagram in schematic form of a process utilizing the present invention.

DESCRIPTION OF THE PREFERRED EMBODIMENTS

The present invention takes advantage of the operating characteristics of catalytic distillation for normally gaseous reactions without operating at the pressures necessary to condense the gases. The advantages of catalytic distillation have become known over the past several years. The success of catalytic distillation lies in an understanding of the principles associated with distillation. First, because the reaction is occurring concurrently with distillation, the initial reaction product is removed from the reaction zone as quickly as it is formed. Second, because the reaction mixture is boiling, the temperature of the reaction is controlled by the boiling point of the mixture at the system pressure. The heat of the reaction simply creates more boil up, but no increase in temperature.

As a result, a great deal of control over the rate of reaction and distribution of products can be achieved by regulating the system pressure. Also, adjusting the through-put (residence time=liquid hourly space velocity) gives further control of product distribution and degree of conversion. The temperature in the reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column.

To change the temperature the pressure is changed. Temperature control in the reaction zone is thus controlled by the pressure; by increasing the pressure, the temperature in the system is increased, and vice versa.

In the present process, pressures of 1 to 50 atmospheres may be used to great effect. Higher pressure can be used, if a more volatile inert is used or for control purposes as described above. Depending on the pressure, inert solvent temperatures in the range of 150° to 300° C. will be observed in the column reactor.

Another advantage, as noted above, is that a condensing liquid reactant occludes a gaseous reactant (such as hydrogen) which perchance improves catalytic contact and lowers the necessary partial pressure of the occluded gaseous reactant.

Heretofore the problem has been that for $H_2$, CO and $CO_2$ the pressures necessary to produce a boiling liquid at the reaction temperature have been too high. The reaction temperature is above the critical temperature of at least the $H_2$. A solution has been found in the use of an inert condensing component which can be used as the boiling liquid. If the inert condensing component is judiciously selected it can have a much higher or much lower boiling point than the reactants or products allowing for easy separation within the distillation column reactor.

In some instances the inert condensing component may be solvent for the gaseous reactants, however, in some instances the inert condensing component is not known as a solvent for the reactants. The proposed mechanism for the present process does not depend on the chemical characteristics of solubility but on the physical characteristics of occlusion. If there is some degree of actual solubility of the gaseous reactants in the condensed inert component, this may enhance the results.

In addition the inert condensing component must be selected such that the boiling point at the desired reaction pressure is the desired reaction temperature. A type of inert component found to be useful in the synthesis of methanol from CO, $CO_2$ and $H_2$ is the general class of $C_7$–$C_{12}$ paraffinic hydrocarbons. A typical example of such is n-octane. Methanol is more soluble in octane at higher temperatures. As the mixture cools the methanol tends to separate into a separate phase for ease of gross separation.

In one embodiment of the present invention the distillation column reactor is operated at the boiling point of the inert condensing component with an overheads being taken and condensed. The reflux of cooler inert condensing component causes some of the evaporated inert condensing component to condense about the gaseous reactants to occlude the gaseous components and carry them to the active catalyst sites where they are present in a more dense form than usual.

Preferably the inert condensing component is both vaporous and liquid within the column, i.e., vaporized in the lower, hotter portion of the column and condensed at least in part in the upper, cooler portion of the column. In one embodiment the inert condensing component is vaporized in a zone of the column containing conventional (non-catalytic) distillation structures and condensed within a catalyst zone of the column containing, for example, catalytic distillation structures. As described above the condensation of the inert condensing component occludes a portion of the gaseous reactants and brings them in contact with the catalyst in the catalyst zone.

Finally, since the reactions are exothermic the boiling of the inert condensing component will remove heat as latent heat of vaporization which can be eventually removed in an overhead condenser. This latter feature is especially useful in temperature control because more heat of reaction only causes more boil up at a given pressure. Therefore the temperature can be simply controlled by the pressure.

Although it is preferred the catalyst zone comprise catalytic distillation structures, catalyst in the catalyst zone may be positioned as shown in U.S. Pat. Nos. 4,847,431; 4,847,430; 4,475,005; 5,338,517; and 5,198,196; all of which are incorporated herein.

When the inert condensing component has a lower boiling point than the products, then the products can be easily separated in the distillation column reactor as bottoms. When the inert solvent has a higher boiling point than the products, the products are taken off the top of the column as condensate or as in this case as an azeotrope with the inert solvent.

Catalytic distillation structures and systems are also described in commonly assigned U.S. Pat. Nos. 4,302,356; 4,439,350; 4,443,559; 5,507,468; 5,189,001; 5,262,012; 5,266,546; 5,348,710; and 5,431,890 all of which are incorporated by reference. In particular the structures disclosed in above referenced patents 5,266,546 and 5,431,890 have been found useful when large amounts of gaseous components such as hydrogen are present.

Basically the patents disclose a solid particulate catalyst surrounded by or contained in a porous component to provide the requisite liquid and vaporous flows and catalyst contact without undue pressure drop.

Catalysts which are useful for the reaction of CO, $CO_2$ and $H_2$ to make methanol contain copper and zinc oxides and may contain other modifiers such as those shown in U.S. Pat. Nos. 4,766,155 and 4,780,481.

One suitable catalyst is United Catalysts Inc.'s C-79, which may be described as comprising copper and zinc oxides on ¼" alumina extrudates.

Since it appears that metallic copper is the active catalyst, it is desirable to reduce the catalyst before use, for example by passing hydrogen gas through the distillation reaction column in the absence of the other components of the reaction system at 200° to 300° C. Preferably the molar ratio C/Zn is 1 or greater than 1, e.g. to 10 and the Al content is 10 or less mol %. Zinc oxide helps in the formation of high copper metal surface area, slows agglomeration of the copper particles, traps Cu poisons and reacts with alumina to inhibit dimethyl ether formation.

It is well known that the presence of $CO_2$ has a positive effect on the rate of methanol formation of the copper/zinc oxide catalyzed reactions. It conditions and prevents damage to the catalyst. Some studies have indicated that essentially all of the methanol is produced from the reaction of $CO_2$ with hydrogen. An internal water gas shift reaction between the resulting water with CO generates more $CO_2$ for methanol production. Without limiting the scope of the invention the following mechanism has been proposed for convenience:

$CO_2 \leftrightarrows CO_2$, ads $H_2 \leftrightarrows 2\ H_{ads}$ $CO_2$, ads+$H_{ads} \leftrightarrows HCOO_{ads}$ $HCOO_{ads}$+3 $H_{ads} \leftrightarrows CH_3OH+O_{ads}$ $CO+O_{ads} \leftrightarrows CO_2$ $H_2+O_{ads} \leftrightarrows H_2O$ An advantage of the instant process is that raw syngas containing higher amounts of CO can be used as feed to the unit without concern for overheating the catalyst. Any additional heat generated will simply cause more boil up.

Referring now to the figure a simplified flow diagram of one embodiment of the invention is depicted. There is shown a distillation column reactor 1 having a bed 2 of supported copper/zinc oxide catalyst prepared as distillation structures. Above the bed 2 is a rectification section 3 containing standard inert distillation structure such as packing, bubble cap trays or sieve trays. Below the bed 2 is a stripping section 4 also containing standard inert distillation structure such as packing, bubble cap trays or sieve trays.

Liquid normal octane is fed to the distillation column reactor 1 via flow line 13 at a point above the catalyst bed 2. The gaseous hydrogen, carbon monoxide and carbon dioxide are fed below the bed 2 via flow line 5. The gaseous hydrogen, carbon monoxide and carbon dioxide rise up into the bed where they are occluded by the condensing and descending normal octane and taken to the catalytic sites on the catalyst. The hydrogen, carbon monoxide and optimally, carbon dioxide react in the bed to form methanol. The distillation column reactor is operated at a pressure such that the normal octane is boiling within the bed.

Methanol and normal octane along with unreacted hydrogen, carbon monoxide and carbon dioxide are taken overhead via flow line 6 and passed through partial condenser 7 where the condensible methanol and normal octane are condensed. The gaseous unreacted hydrogen, carbon monoxide and carbon dioxide are separated from the liquid methanol and normal octane in separator 14 and removed via flow line 11 for recycle to the reactor 1 (not shown).

Due to cooling, a phase separation between the methanol and normal octane occurs in the separator allowing the methanol to be withdrawn via flow line 12 and normal octane to be withdrawn via flow line 9 to be returned to the distillation column reactor.

A bottoms draw is taken from the distillation column reactor 1 via flow line 10 to remove any impurities, heavy byproducts, and to purge excess normal octane.

EXAMPLE 1

In the following example a one inch diameter 30 foot tall distillation column reactor was used. Five feet of ceramic packing was placed in the reactor to support fifteen feet of a CuO/ZnO catalyst (0.9 lb.) prepared as a distillation structure. The reactor was topped off with another five feed of ceramic packing. The catalyst used was commercially available UCI C-79 methanol catalyst in the form of ¼ inch extrudates. The catalyst was placed in the structure described in U.S. Pat. No. 5,431,890 which essentially consists of flexible, semi-rigid open mesh tubular elements filled with a particulate catalytic material (catalyst component) and sealed at both ends, intimately associated with and supported by a wire mesh screen.

Pure hydrogen and CO were used to simulate the syngas feed and were fed to the bottom of the reactor. The $CO_2$ was introduced into the reactor as a solution in the n-octane. The $CO_2$ was used as a pressure head in the n-octane feed tank in place of nitrogen. The resultant $CO_2$ concentrations in the reactor were in the range of 10–20%. Thus $CO_2$ does not have a flow rate.

The n-octane/$CO_2$ mix was fed at the top of the catalyst section and the $H_2$/CO mix was fed to the bottom of the reactor. Column pressures were controlled in the 300–500 psig range resulting in column temperatures in the 350°–650° F. range. The product methanol was taken off the top of the column as it forms an azeotrope with the octane solvent. No continuous bottoms draw was taken except for periodic removal of small amounts to minimize the accumulation of any heavies in the reboiler. The results are reported in TABLE II.

TABLE II

| RUN 1 Run Time, hr | 0–250 | 250–300 | 300–350 | 350–400 | 400–450 |
|---|---|---|---|---|---|
| Octane feed, lbs/hr | 0.5 | 0.7 | 0.9 | 0.5 | 1.2 |
| $H_2$ Feed, SCFH | 8–12 | 10 | 10 | 10 | 10 |
| CO feed, SCFH | 4 | 4 | 5 | 5 | 5 |
| lbs/hr | 0.32 | .032 | 0.4 | 0.4 | 0.4 |
| Overhead rate, lbs/hr | 0.5 | 0.65 | 0.85 | 0.55 | 1.0 |
| Methanol phase, % of Overhead | 25 | 25 | 20 | 20 | 15 |
| Pressure, psig | 300 | 350 | 350 | 400 | 400 |
| Bottom Temp., °F. | 560 | 580 | 580 | 610 | 610 |
| Methanol Prod., lbs/hr | 0.11 | 0.14 | 0.15 | 0.94 | 0.13 |
| CO Conversion, % | 34 | 43 | 36 | 24 | 32 |
| Methanol Productivity, lbs/hr/lb catalyst | 0.12 | 0.15 | 0.17 | 0.11 | 0.14 |

| RUN 2 Run Time, hr | 0–100 | 100–140 | 140–165 |
|---|---|---|---|
| Octane feed, lbs/hr | 0.6 | 0.6 | 0.6 |
| $H_2$ Feed, SCFH | 12 | 12 | 12 |
| CO feed, SCFH | 4–6 | 6 | 6 |
| lbs/hr | 0.4 | 0.5 | 0.5 |
| Overhead rate, lbs/hr | 0.5 | 0.5 | 0.5 |
| Methanol phase, % of Overhead | 20 | 20–40 | 40 |
| Pressure, psig | 300 | 400 | 500 |
| Bottom Temp., °F. | 550 | 610 | 660 |
| Methanol Prod., lbs/hr | 0.09 | 0.09–0.17 | 0.20 |
| Co Conversion, % | 21 | 21–34 | 34 |
| Methanol Productivity, lbs/hr/lb catalyst | 0.09 | 0.09–0.17 | 0.20 |

Mass balance data was collected on RUN 2 and as the results in Table III show there was a good balance between materials in and materials out.

TABLE III

| MATERIAL BALANCE | | |
|---|---|---|
| | (60–120 hr) | (130–160 hr) |
| FEEDS | | |
| CO (gms/hr) | 325 | 225 |
| $H_2$ (gms/hr) | 31 | 31 |
| PRODUCTS | | |
| MEOH in MEOH Phase (lbs/hr) | 0.085 | 0.205 |

TABLE III-continued

MATERIAL BALANCE

|  | (60–120 hr) | (130–160 hr) |
|---|---|---|
| MEOH in Octane Phase (lbs/hr) | 0.02 | 0.015 |
| Total MEOH (lbs/hr) | 0.105 (48 gms) | 0.22 (91 gms) |
| CO (gms/hr) in MEOH product | 42 | 80 |
| $H_2$ (gms/hr) in MEOH product | 6 | 11 |
| % Conversion of CO | 18.7% | 35.6% |
| VENT ANALYSIS | | |
| $H_2$ | 8% (22 gms) | 8% (22 gms) |
| CO | 65% (177 gms) | 60% (163 gms) |
| $CO_2$ | 20% (54 gms) | 25% (65 gms) |
| $N_2$ | 7% | 7% |
| MATERIAL BALANCE (on CO + $H_2$ FEEDS gms/hr | 256 | 256 |
| MEOH product gms/hr | 48 | 91 |
| Vent calculated | 208 | 165 |
| Vent measured | 199 | 185 |

EXAMPLE 2

This example was carried out to assess the effect of catalyst particle size (surface area). The catalyst pellets previously described were crushed and screened. The −10 to +40 mesh particles were used as packing to make the distillation structure. The data shows that a substantial increase in MeOH productivity can be obtained with higher surface area. The conditions and results are reported in Table IV below.

TABLE IV

PROCESS CONDITIONS

| Run Time Period (hrs) | 0–75 | 75–210 | 210–260 | 260–350 | 350–450 |
|---|---|---|---|---|---|
| Octane Feed Rate lbs/hr | 0.6 | 0.6 | 0.6 | 1.0 | 1.5 |
| $H_2$ Feed (scfh) | 10 | 10 | 15 | 15–20 | 20 |
| CO Feed schf (lbs) | 4 (0.32) | 5 (0.4) | 5 (0.4) | 8 (0.6) | 10 (0.8) |
| OH Rate (schf) | 0.5 | 0.5 | 0.5 | 0.7 | 1.4 |
| % of OH (MeOH Phase) | 20 | 60 | 50 | 25 | 10 |
| Pressure (psi) | 300 | 400 | 500 | 500–400 | 400 |
| Bot. Temp (°F.) | 550 | 550 | 600 | 600–550 | 550 |
| Col. Temp (°F.) | 400–450 | 300–450 | 350–450 | 350–500 | 350–500 |
| MeoH Product (#/hr) | 0.09 | 0.26 | 0.21 | 0.15 | 0.12 |
| % Conversion | 28 | 65 | 53 | 25 | 15 |
| (MeoH productivity lbs/hr catalyst/hr based on 0.9# catalyst charge) | 0.1 | 0.29 | 0.23 | 0.16 | 0.13 |

The invention claimed is:

1. A process for the production of methanol comprising the steps of:

(a) feeding an inert condensing component as a liquid stream to a distillation column reactor having a distillation reaction zone, said inert condensing component boiling at the conditions within said distillation column reactor;

(b) feeding carbon monoxide and hydrogen or carbon monoxide, carbon dioxide and hydrogen to a distillation column reactor, and (c) concurrently in said distillation column reactor:

(i) boiling said inert condensing component and refluxing said inert condensing component such that a portion of said inert component is condensing in said distillation reaction zone;

(ii) contacting said CO and $H_2$ or CO, $CO_2$ and $H_2$ and said inert condensing component with a solid particulate catalyst in said distillation reaction zone, under conditions within said reactor at which said CO, $CO_2$ and $H_2$ are in the vapor state, and reacting a portion of said CO and/or $CO_2$ and $H_2$ to form methanol, and (iii) removing an overheads containing methanol, inert condensing agent and unreacted CO, $CO_2$ or hydrogen and (d) separating said methanol from said carbon monoxide, carbon dioxide or hydrogen.

2. The method according to claim 1 wherein said inert condensing component has a higher boiling point than methanol and said methanol is removed from said distillation column reactor as overheads along with said inert component.

3. The method according to claim 2 wherein said overheads are cooled to condense said inert condensing component and said methanol is substantially separated from said inert condensing component in a separator drum.

4. The method according to claim 1 wherein said inert condensing component and any unreacted carbon monoxide, carbon dioxide and hydrogen are taken as overheads and said overheads are cooled to condense said inert component and said carbon monoxide, carbon dioxide and hydrogen are separated from said inert component in a separator drum.

5. The process according to claim 1 wherein at least some of said carbon monoxide, carbon dioxide and hydrogen are at least partially soluble in said inert condensing component.

6. The process according to claim 1 wherein said solid particulate catalyst is prepared as a catalytic distillation structure.

7. The process according to claim 6 wherein said solid particulate catalyst comprises copper and zinc oxides.

8. The process according to claim 1 wherein said inert condensing component comprises $C_7$–$C_{12}$ paraffinic hydrocarbons.

9. The process according to claim 7 wherein said copper and zinc oxides are reduced prior to introduction of feed.

10. The process according to claim 1 wherein methanol is more soluble in said inert condensing component at the temperatures in the distillation column reactor than at lower temperatures and said methanol and inert condensing component are taken as overheads from said distillation column reactor.

11. The method according to claim 1 wherein said overheads are cooled to condense said inert condensing component and said methanol and said methanol is separated from said inert condensing component in a separator drum by a phase separation of said methanol and said inert condensing component.

12. The process according to claim 1 wherein said inert condensing component comprises n-octane.

13. A process for the production of methanol comprising the steps of:

(a) feeding normal octane as a liquid stream to a distillation column reactor having a distillation reaction zone, said normal octane boiling at the conditions within said distillation column reactor;

(b) feeding carbon monoxide and hydrogen or carbon monoxide, carbon dioxide and hydrogen to a distillation column reactor, said carbon monoxide, carbon dioxide and hydrogen being vapors at the conditions within said reactor; and (c) concurrently in said distillation column reactor
  (i) boiling and refluxing said normal octane such that a portion of said normal octane is condensing in said distillation reaction zone;
  (ii) contacting said normal octane and said carbon monoxide and hydrogen or carbon monoxide, carbon dioxide and hydrogen with a solid particulate catalyst in said distillation reaction zone thereby reacting a portion of said carbon monoxide and/or carbon dioxide and hydrogen to form methanol, and
  ((iii) removing an overheads containing methanol, normal octane and unreacted CO, $CO_2$ or hydrogen;

(d) separating said methanol from said carbon monoxide, carbon dioxide or hydrogen, and (e) cooling said overheads to condense said normal octane and said methanol thereby causing a substantial liquid phase separation of said methanol from said normal octane.

14. The process according to claim 13 wherein said solid particulate catalyst comprises copper and zinc oxides on an alumina base.

15. The process according to claim 14 wherein said copper and zinc oxides are reduced prior to introduction of feed.

* * * * *